(12) United States Patent
Chaix et al.

(10) Patent No.: US 9,540,405 B2
(45) Date of Patent: Jan. 10, 2017

(54) DIAMINOPHENOTHIAZINIUM DERIVATIVES FOR LABELLING BIOMOLECULES, METHOD AND SUBSTRATE FOR LABELLING OLIGONUCLEOTIDES, AND OLIGONUCLEOTIDES OBTAINED

(71) Applicants: UNIVERSITE CLAUDE BERNARD LYON I, Villeurbanne (FR); CENTRE NATIONAL DE LA RECHERCHE SCIENTIFIQUE, Paris (FR)

(72) Inventors: Carole Chaix, Chaponnay (FR); Gabriel De Crozals, Lyons (FR)

(73) Assignees: UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 35 days.

(21) Appl. No.: 14/379,417

(22) PCT Filed: Feb. 21, 2013

(86) PCT No.: PCT/FR2013/050356
§ 371 (c)(1),
(2) Date: Aug. 18, 2014

(87) PCT Pub. No.: WO2013/128099
PCT Pub. Date: Sep. 6, 2013

(65) Prior Publication Data
US 2015/0011712 A1 Jan. 8, 2015

(30) Foreign Application Priority Data

Feb. 27, 2012 (FR) ..................... 12 51739

(51) Int. Cl.
C07D 279/18 (2006.01)
C07F 9/6547 (2006.01)
C07H 1/00 (2006.01)
C07H 21/00 (2006.01)
C09B 21/00 (2006.01)

(52) U.S. Cl.
CPC ........... *C07F 9/6547* (2013.01); *C07D 279/18* (2013.01); *C07H 1/00* (2013.01); *C07H 21/00* (2013.01); *C09B 21/00* (2013.01)

(58) Field of Classification Search
None
See application file for complete search history.

(56) References Cited

U.S. PATENT DOCUMENTS 7,301,041 B2  11/2007  Chaix-Bauvais et al.
2005/0038234 A1  2/2005  Chaix-Bauvais et al.

FOREIGN PATENT DOCUMENTS

WO    03068787 A1    8/2003

OTHER PUBLICATIONS

Efimov et al., "Application of new catalytic phosphate protecting groups for the highly efficient phosphotriester oligonucleotide synthesis", Nucleic Acids Research, vol. 14, No. 16(1986), p. 6525-6540.
Farjami et al., "DNA interactions with a Methylene Blue redox indicator depend on the DNA length and are sequence specific", The Royal Society of Chemistry 2010, 135, p. 1443-1448.
Froehler et al., "Nucleoside H-Phosphonates: Valuable Intermediates in the Synthesis of Deoxyoligonucleotides", Tetrahedron Letters. vol. 27, No. 4, p. 469-472, 1986.
Rowe et al., "Electrochemical Biosensors Employing an Internal Electrode Attachment Site and Achieving Reversible, High Gain Detection of Specific Nucleic Acid Sequences", Analytical chemistry 2011, 83, p. 9462-9466.
Mills et al., "Effect of alkali on methylene blue (C.I. Basic Blue 9) and other thiazine dyes", Dyes and Pigments 88 (2011), p. 149-155.
International Search Report mailed Apr. 15, 2013, corresponding to International Application No. PCT/FR2013/050356.
Majken N. Hansen et al.: "Synthesis and Application of a Triazene-Ferrocene Modifier for Immobilization and Characterization of Oligonucleotides at Electrodes", The Journal of Organic Chemistry, vol. 75, No. 8 (2010), pp. 2474-2481.
Judith Jahnchen et al.: "NMR studies on self-complementary oligonucleotides conjugated with methylne blue", Biopolymers, vol. 79, No. 6, (2005), pp. 335-343.
Uwe Moeller et al.: "Versatile Procedure of Multiple Introduction of 8-Aminomethylene Blue into Oligonucleotides", Bioconjugate Chemistry, vol. 6, No. 2 (1995), pp. 174-178.
F. Schubert et al.: "Covalent Attachment of Methylene Blue to Oligonucleotides", Nucleosides and Nucleotides, vol. 14, No. 6(1995), pp. 1437-1443.

*Primary Examiner* — Alicia L Otton
(74) *Attorney, Agent, or Firm* — Ladas & Parry LLP

(57) ABSTRACT

The present invention relates to diaminophenothiazinium derivatives of formula (I); in which $R_1$, $R_2$, $R_3$, $R_4$, $R_5$, $R_6$ and $X^-$ are as defined in Claim 1, and also the methods for labelling oligonucleotides using such a derivative, labeling substrates and the oligonucleotides which can be obtained by means of such methods or from such labelling substrates.

19 Claims, 1 Drawing Sheet

DIAMINOPHENOTHIAZINIUM DERIVATIVES FOR LABELLING BIOMOLECULES, METHOD AND SUBSTRATE FOR LABELLING OLIGONUCLEOTIDES, AND OLIGONUCLEOTIDES OBTAINED

This application is a 371 of PCT/FR2013/050356, filed on Feb. 21, 2013, which claims priority to French Application No. 1251739, filed Feb. 27, 2012.

The present invention relates to the technical field of biomolecule labels. More specifically, the present invention relates to novel diaminophenothiazinium derivatives of the same family as methylene blue, and having a structure suitable for being able to be incorporated into oligonucleotides, directly during the synthesis thereof. The subject of the invention is also the methods for growing oligonucleotides using such derivatives, the resulting oligonucleotides and synthesis substrates for oligonucleotides onto which diaminophenothiazinium derivatives are grafted.

Methylene blue is a molecule with many properties. It is, inter alia, an electroactive molecule which has the property of changing from a reduced state to an oxidized state under the action of an oxidation potential, while releasing 2 electrons (Farjami, E.; Clima, L.; Gothelf, K. V.; Ferapontova, E. E. Analyst 2010, 135, 1443-1448). Methylene blue is also a colored molecule, which absorbs at the wavelength of 665 nm in aqueous medium, and a fluorescent molecule, the excitation wavelength of which is 665 nm and the emission wavelength of which is 682 nm.

For all these reasons, methylene blue is a very effective biological label, whether for carrying out an optical detection or an electrochemical detection of the labeled biological entity.

In the 1980s, solid-phase syntheses of biomolecules and in particular of peptides and of oligonucleotides were developed. The chemical process currently most widely used for the synthesis of oligonucleotides is known as "the phosphoramidite method". This method consists in sequentially adding a single nucleotide at a time to a growing chain of oligonucleotides. A group which protects hydroxyl functions under oligonucleotide synthesis conditions, for instance a dimethoxytrityl group, is placed at the 5' end of a growing oligonucleotide chain which is itself attached, via its 3' end, to a solid substrate. This protective group is removed by virtue of an acid treatment, for example with trichloroacetic acid, and the 5' end of the oligonucleotide thus freed is then coupled with a nucleotide synthon substituted at its 3' end with a phosphoramidite derivative, thereby making it possible to increase the nucleotide chain. The agent for activating the coupling reaction is, for example, tetrazole which reacts with the phosphoramidite function of the synthon, forming in situ an intermediate that is very reactive with respect to the deprotected alcohol function present at the 5' end of the oligonucleotide attached to the substrate. It is also possible to use, in place of a phosphoramidite group, a phosphodiester group (Reese C. B., Titmas R. C., Yau L., Tetrahedron Let. 1978, 30, 2727-2730; Efimov, V. A., Burgakova, A. A., Dubey, I. Y., Polushin, N. N., Chakhmakhcheva, O. G., Orchinnikov, Y. A., Nucl. Acids, Res., 1986, 14, 6525-6540) or a hydrogen phosphonate group (Froehler, B. C., Matteucci, M. D. Tetrahedron Let. 1986, 27, 469-472). For further details regarding these techniques, reference may be made to Current Protocols in Nucleic Acid Chemistry, Volume 1, Editors: S. L. Beaucage, D. E. Bergstrom, G. D. Glick, R. A. Jones, John Wiley & Sons, Inc., 2004; Protocols for oligonucleotides and analogs, Volume 20, Editor: S. Agrawal, Methods in molecular biology, Humana Press, 1993. It is advantageous to introduce at this stage modified nucleotide synthons containing, for example, a label of fluorescent or electrochemical type.

In automatic synthesizers, the sequence of a reaction can be repeated a large number of times, for example up to 150 times. As soon as an oligonucleotide of desired sequence is synthesized, it is released from the substrate by means of a basic treatment which also makes it possible to remove the various protective groups. The oligonucleotide obtained can then be purified by HPLC or by gel electrophoreses.

Solid-phase oligonucleotide synthesis chemistry therefore requires a final step of deprotection of the nucleotides forming the oligonucleotide and of detachment from the substrate, in a basic medium, typically in an aqueous 30% by volume $NH_4OH$ solution or an aqueous 0.05M $K_2CO_3$ solution. These treatments are not compatible with prior grafting of methylene blue onto the oligonucleotide during its synthesis, since methylene blue is a phenothiazine substituted with two dimethylamines, which is not stable in a basic medium. Indeed, the dimethylamine groups are rapidly cleaved in a basic medium, resulting in loss of the electrochemical and coloring properties (Mills A., Hazafy D., Parkinson J., Tuttle T., Hutchings M. G., Effect of alkali on methylene blue (C.I. Basic Blue 9) and other thiazine dyes, Dyes and Pigments 2011, 88, (2), 149-155).

To date, the strategies proposed for grafting a methylene blue derivative onto a biomolecule of the oligonucleotide type involve post-synthesis coupling to the biomolecule, i.e. coupling during a final step to the biomolecule already formed. An activated ester derivative of methylene blue has been synthesized so as to be coupled to a biomolecule bearing primary amine functions (Jähnchen J., Purwanto M. G. M., Weisz K., NMR studies on self-complementary oligonucleotides conjugated with methylene blue, Biopolymers 2005, 79, (6), 335-343; Farami, Anal. Chem. 2011; Hansen, JOC, 2010). The studies by Rowe et al. (Aaron Rowe, Kelly N Chuh, Arica A Lubin, Erin A Miller, Brett M Cook, Daniel N Hollis, and Kevin W. Plaxco, Anal. Chem. 2011, 83 (24), 9462-9466) for their part provide for grafting of methylene blue onto an already formed oligonucleotide by virtue of a peptide linker or a hydrazone linker. An 8-amino methylene blue derivative has also been described for carrying out coupling to a polymer bearing acid functions (Uwe Moller, Frank Schubert, and Dieter Cech, Bioconjugate, 1995, 6, 174-178).

Generally, it has been considered in the prior art that methylene blue must be coupled in the very last step of the synthesis, in order to limit the risks of degradation encountered in excessively aggressive media using a base or a reducing agent used in the syntheses of biomolecules, and in particular in the case of the synthesis of oligonucleotides.

In the context of the invention, the inventors provide novel diaminophenothiazinium derivatives which can be directly integrated into biomolecules, and in particular into oligonucleotides during their synthesis.

In this context, the present invention relates to diaminophenothiazinium derivatives of formula (I):

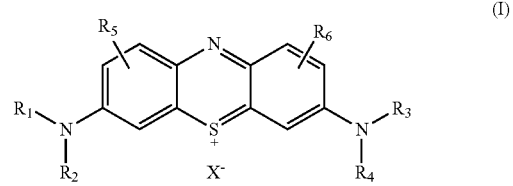

in which:
one of the $R_1$, $R_2$, $R_3$ and $R_4$ groups represents $-A_1-OR_7$, with $A_1$ representing a linear or branched alkylene chain comprising from 2 to 12 carbons, the oxygen and nitrogen atoms being separated by at least two consecutive carbon atoms, and $R_7$ representing a phosphorus-comprising group capable of reacting with a free hydroxyl under oligonucleotide synthesis conditions, said group preferably forming, with $OA_1$ to which it is bonded, a phosphoramidite, phosphodiester or hydrogen phosphonate group, the other $R_1$, $R_2$, $R_3$ and $R_4$ groups, which may be identical or different, represent, independently of one another:

an -$A_2$-$OR_8$ group, with $A_2$ representing a linear or branched alkylene chain comprising from 2 to 12 carbons, the oxygen and nitrogen atoms being separated by at least two consecutive carbon atoms, and $R_8$ representing a group which protects hydroxyl functions under oligonucleotide synthesis conditions, preferably chosen from trityl, 4-O-monomethoxytrityl, 4,4'-O-dimethoxytrityl, tert-butyldimethylsilyl, acetyl, trifluoroacetyl, 9-phenylxanthen-9-yl and fluorenylmethyloxycarbonyl groups, an alkyl group having from 2 to 12 carbon atoms, or else $R_1$ and $R_2$ or $R_3$ and $R_4$ are bonded to one another to form, with the nitrogen atom to which they are bonded, a piperidinyl or pyrrolidinyl group, $R_5$ and $R_6$, which may be identical or different, represent, independently of one another, a hydrogen, chlorine, bromine, iodine or fluorine atom, or an alkyl group having from 1 to 12 carbon atoms, an alkenyl group having from 2 to 12 carbon atoms, an alkynyl group having from 2 to 12 carbon atoms, an acyl group or a phenyl group, $X^-$ represents an anion, preferably chosen from $Cl^-$, $I^-$, $ClO_4^-$ and $NO_3^-$.

In the context of the invention, the dimethylamine groups of the methylene blue have been replaced with chains which are longer and more hindered, in order to obtain a methylene blue derivative which, once integrated into an oligonucleotide, is more stable, in particular under basic conditions. Such a derivative is therefore compatible with use in the synthesis of supported oligonucleotides which require, in a final step, a basic treatment in order to release the formed oligonucleotide from the synthesis substrate and/or to deprotect the nucleotides.

Furthermore, it has also been noted that these chemical modifications do not affect, in a problematic manner, the oxidoreductive properties of the resulting diaminophenothiazinium derivatives, thus confirming their value for labeling oligoncleotides, or even other biomolecules such as peptides.

According to the embodiments which are preferred, in particular in terms of stability, $A_1$ and $A_2$ (when it is present) are linear or branched alkylene chains in which from 2 to 6 consecutive carbon atoms separate the oxygen and nitrogen atoms.

In the context of the invention, it is possible that three of the $R_1$, $R_2$, $R_3$ and $R_4$ groups represent an -$A_2$-$OR_8$ group as defined in the invention. In this case, it is possible to graft several nucleotides onto the same diaminophenothiazinium derivative, thereby making it possible to synthesize branched oligonucleotides. According to other embodiments, at least one of the $R_1$, $R_2$, $R_3$ and $R_4$ groups does not represent an -$A_2$-$OR_8$ group and said $R_1$, $R_2$, $R_3$ or $R_4$ group(s) different than -$A_1$-$OR_7$ and than -$A_2$-$OR_8$ represent(s) an alkyl group having from 2 to 12 carbon atoms, preferably from 4 to 12 carbon atoms. In this case, the diaminophenothiazinium derivatives can correspond to one of the formulae given hereinafter:

formula (Ia):

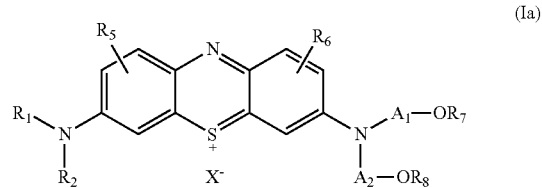

in which:

$A_1$, $A_2$, $R_5$, $R_6$, $R_7$, $R_8$ and $X^-$ are as defined for the compounds of formula (I), $R_1$ and $R_2$, which may be identical or different, represent, independently of one another, an alkyl group having from 2 to 12 carbon atoms, preferably from 4 to 12 carbon atoms, or $R_1$ and $R_2$ are bonded to one another to form, with the nitrogen atom to which they are bonded, a piperidinyl or pyrrolidinyl group;

formula (Ib):

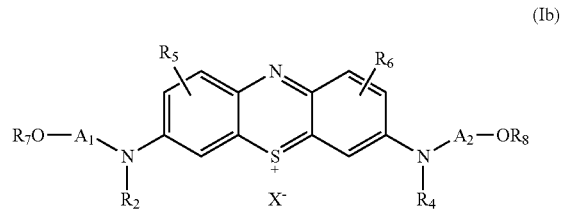

in which:

$A_1$, $A_2$, $R_5$, $R_6$, $R_7$, $R_8$ and $X^-$ are as defined for the compounds of formula (I), $R_2$ and $R_4$, which may be identical or different, represent, independently of one another, an alkyl group having from 2 to 12 carbon atoms, preferably from 4 to 12 carbon atoms; and formula (Ic):

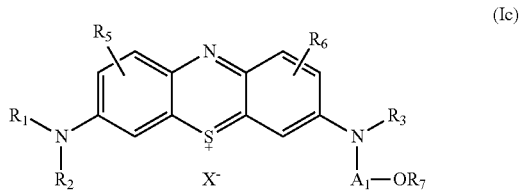

in which:

$A_1$, $R_5$, $R_6$, $R_7$ and $X^-$ are as defined for the compounds of formula (I), $R_1$ and $R_2$, which may be identical or different, represent, independently of one another, an alkyl group having from 2 to 12 carbon atoms, preferably from 4 to 12 carbon atoms, or $R_1$ and $R_2$ are bonded to one another to form, with the nitrogen atom to which they are bonded, a piperidinyl or pyrrolidinyl group, $R_3$ represents an alkyl group having from 2 to 12 carbon atoms, preferably from 4 to 12 carbon atoms.

Whatever the compound of formula (I), (Ia), (Ib) or (Ic) previously described, $R_5$ and $R_6$ represent, for example, a hydrogen atom, as in the case of methylene blue.

The R$_7$ group may be of the type —P(NR'aR'b)R'c (and therefore forms a phosphoramidite with —OA$_1$-), —P(O)(OH)(OR'd) (and therefore forms a phosphodiester with —OA$_1$-) or —P(O)(OH)H (and therefore forms a hydrogen phosphonate with —OA$_1$-), in which R'a, R'b, R'c and R'd are, for example, optionally substituted alkyl or phenyl groups. Advantageously, in the compounds of formulae (I), (Ia), (Ib) and (Ic) previously described, one of the R$_1$, R$_2$, R$_3$ and R$_4$ groups represents an -A$_1$-OR$_7$ group in which R$_7$ represents a —P[N($^i$Pr)$_2$](OCH$_2$CH$_2$C≡N) (with $^i$Pr=isopropyl) and therefore forms a phosphoramidite with OA$_1$, and A$_1$ is as previously defined. R$_7$ may more generally represent a —P{N[(C$_2$-C$_{12}$)alkyl]$_2$}(OCH$_2$CH$_2$C≡N) group. R$_7$ may also represent a group such as O-(2-chlorophenyl phosphate) or O-2-(1-methylimidazol-2-yl)phenyl phosphate, so as to form a phosphodiester with OA$_1$, R$_7$ may also represent a —P(O)(OH)H group.

Such diaminophenothiazinium derivatives may be prepared according to techniques well known to those skilled in the art, in particular by analogy with the techniques described in the examples. Essentially, it is possible to form amino derivatives of phenothiazinium by reacting, in particular at ambient temperature, a phenothiazinium salt, such as phenothiazinium tetraiodide, with a dialkylamine, a dihydroxyalkylamine or an alkyl(hydroxyalkyl)amine in an alcohol such as methanol or a chlorinated solvent such as dichloromethane.

The amine/phenothiazinium salt molar ratio will be approximately equal to 2 when it is desired to graft a single amine onto the ring and will be greater than 2 when it is desired to graft two identical amines on either side of the phenothiazinium ring (in the case of the compounds of formula (Ib) in which A$_1$=A$_2$ and R$_2$=R$_4$). For the compounds in which it is necessary to graft two different amines on either side of the phenothiazinium ring (in the case of the compounds (Ia) and of the compounds (Ib) in which A$_1$ is different than A$_2$ and/or R$_2$ is different than R$_4$), a new reaction will be carried out with another amine under analogous conditions. At least one of the amines used is substituted with a hydroxyalkyl group. A coupling is then carried out on the hydroxyl function with at least one halogenated derivative, and in particular a chlorinated derivative Cl—R$_7$ or Cl—R$_8$, so as to obtain the desired —O—R$_7$ or —O—R$_8$ function. Such a coupling is carried out under conditions well known to those skilled in the art, in particular in the presence of diisopropylethylamine in acetonitrile. Two successive couplings may be carried out in order to obtain two different functionalizations, in the case where at least two hydroxyl functions are present.

The derivatives according to the invention may be integrated into an oligonucleotide, in a conventional supported synthesis process, in place of a nucleotide.

The term "oligonucleotide" denotes a series of at least two natural or modified nucleotides (deoxyribonucleotides or ribonucleotides, or both) capable of hybridizing, under appropriate hybridization conditions, with an at least partially complementary oligonucleotide. The term "nucleotide" is intended to mean an organic compound consisting of a purine or pyrimidine base bonded to a monosaccharide (ribose or deoxyribose) and to a phosphate group. The term "modified nucleotide" is intended to mean, for example, a nucleotide comprising a modified base and/or comprising a modification at the level of the internucleotide bond and/or at the level of the backbone. By way of example of a modified base, mention may be made of inosine, methyl-5-deoxycytidine, dimethylamino-5-deoxyuridine, 2,6-diaminopurine and bromo-5-deoxyuridine. In order to illustrate a modified internucleotide bond, mention may be made of phosphorothioate, N-alkylphosphoramidate, alkyl phosphonate and alkyl phosphotriester bonds.

A subject of the present invention is also a method for labeling an oligonucleotide with a diaminophenothiazinium derivative according to the invention, which comprises the growth of an oligonucleotide grafted onto a solid substrate, and the replacement of one or more nucleotides with one or more of said diaminophenothiazinium derivatives according to the invention, before the oligonucleotide is detached from the solid substrate. At least one substitution with a diaminophenothiazinium derivative can be carried out in the 3' or 5' positions, on the first or the last nucleotide, respectively. It is also possible to carry out the insertion of a diaminophenothiazinium derivative inside the nucleotide chain, the replacement of a phosphoramidite, phosphodiester or hydrogen phosphonate nucleotide synthon with a diaminophenothiazinium derivative according to the invention then being carried out before the end of the growth of the oligonucleotide. In the context of the invention, it is possible to insert the diaminophenothiazinium derivative at any place on the nucleotide chain, given that said derivative can be introduced directly during the growth of the oligonucleotides. It is possible to incorporate a diaminophenothiazinium derivative according to the invention on any position of an oligonucleotide sequence. Furthermore, it is possible to incorporate a large number of diaminophenothiazinium derivatives within an oligonucleotide sequence, by supported synthesis. According to one particular embodiment, at least two insertions, for example consecutive insertions, are carried out. It should be noted that such a labeling process was already described in application WO 03/068787 in the case of a ferrocene derivative. Nevertheless, the replacement of a label of the ferrocene type with a diaminophenothiazinium derivative will be able to provide a notable improvement, in terms of labeling performance. Indeed, the labels according to the invention transfer two electrons per oxidation wave, instead of one electron transferred in the case of ferrocene. The diaminophenothiazinium derivatives are also more stable with respect to oxidizing conditions and more sensitive to their stearic and ionic environment, in the medium.

A subject of the present invention is also the labeled oligonucleotides which can be obtained by means of the labeling method according to the invention or from the substrates described hereinafter.

The diaminophenothiazinium derivatives according to the invention are highly reactive and can also be used to react efficiently with another type of biomolecule, polymer or a planar or particulate substrate, bearing alcohol or amine functions in particular.

The invention also relates to the oligonucleotide synthesis substrates comprising at least one diaminophenothiazinium derivative covalently grafted at the surface of the substrate and corresponding to the formula:

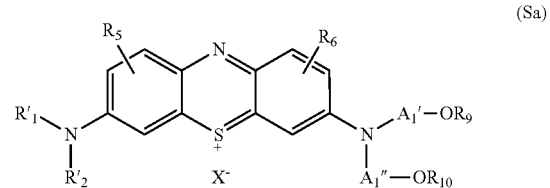

in which:

R$_5$, R$_6$ and X$^-$ are as defined for the compounds of formula (I),

R'$_1$ and R'$_2$, which may be identical or different, represent, independently of one another, an alkyl group having from 2 to 12 carbon atoms, preferably from 4 to 12 carbon atoms, or R$_1$ and R$_2$ are bonded to one another to form, with the nitrogen atom to which they are bonded, a piperidinyl or pyrrolidinyl group, A$_1$' and A$_1$", which may be identical or different, represent, independently of one another, an A$_1$ chain as defined for the compounds of formula (I), and R$_9$ represents a group which protects hydroxyl functions under the conditions conventionally used in the synthesis of oligonucleotides, preferably chosen from trityl, 4-O-monomethoxytrityl, 4,4'-O-dimethoxytrityl, tert-butyldimethylsilyl, acetyl, trifluoroacetyl, 9-phenylxanthen-9-yl and fluorenyl,ethyloxycarbonyl groups; and R$_{10}$ represents —CO-A$_3$-CO—NH-Substrate, with A$_3$ representing a linear or branched alkylene chain comprising from 1 to 6 carbon atoms; or

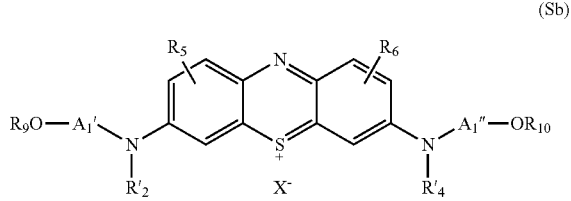

(Sb)

in which:
R$_5$, R$_6$ and X$^-$ are as defined for the compounds of formula (I), R'$_2$ and R'$_4$, which may be identical or different, represent, independently of one another, an alkyl group having from 2 to 12 carbon atoms, preferably from 4 to 12 carbon atoms, A$_1$' and A$_1$", which may be identical or different, represent, independently of one another, an A$_1$ chain as defined for the compounds of formula (I), and R$_9$ represents a group which protects hydroxyl functions under the conditions conventionally used in the synthesis of oligonucleotides, preferably chosen from trityl, 4-O-monomethoxytrityl, 4,4'-O-dimethoxytrityl, tert-butyldimethylsilyl, acetyl, trifluoroacetyl, 9-phenylxanthen-9-yl and fluorenylmethyloxycarbonyl groups; and R$_{10}$ represents —CO-A$_3$-CO—NH-Substrate, with A$_3$ representing a linear or branched alkylene chain comprising from 1 to 6 carbon atoms.

The substrate may in particular be chosen from resins, in particular from resins based on polystyrene, polyacrylamide, polyethylene glycol, cellulose, polyethylene, polyester, latex, polyamide, polydimethylacrylamide, synthetic or natural hydrophilic polymers, glasses and silicas with a controlled porosity, glass beads or silica gels. This type of substrate generally comprises surface amine functions which will be modified so as to reveal surface acid functions which will then be able to be coupled to hydroxyalkylamino functions borne by the heterocycle so as to result in substrates (Sa) and (Sb) above.

Certain definitions used in the description of the invention are recalled.

The term "alkyl" is intended to mean a linear or branched, saturated monovalent hydrocarbon-based group. By way of examples of an alkyl group, mention may be made of methyl, ethyl, n-propyl, isopropyl, n-butyl, isobutyl, sec-butyl, t-butyl, n-pentyl and n-hexyl groups.

The term "alkenyl" is intended to mean a linear or branched, unsaturated monovalent hydrocarbon-based group comprising at least one double bond.

The term "alkynyl" is intended to mean a linear or branched, unsaturated monovalent hydrocarbon-based group, comprising at least one triple bond.

The term "alkylene" is intended to mean a linear or branched, saturated divalent hydrocarbon-based group. By way of example of an alkylene group comprising from 2 to 12 carbon atoms, mention may be made of —(CH$_2$)$_2$—, —CH$_2$—CH(CH$_3$)—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —CH$_2$—CH(CH$_2$CH$_3$)—, —(CH$_2$)$_2$—CH(CH$_2$CH$_3$)—, etc.

The expression "the oxygen and nitrogen atoms being separated by at least two consecutive carbon atoms" means that a linear alkylene chain comprising at least two carbon atoms separates the oxygen atom from the nitrogen atom (at least the series —N—C—C—O— therefore exists), it being possible for the other carbon atoms, in the case of a branched alkylene chain comprising more than two carbon atoms, to then be on the branches.

An example of a group which protects hydroxyl functions under oligonucleotide synthesis conditions is, for example, chosen from trityl, 4-O-monomethoxytrityl, 4,4'-O-dimethoxytrityl, tert-butyldimethylsilyl, acetyl, trifluoroacetyl, 9-phenylxanthen-9-yl (pixyl) (the pixyl protective group is described in particular in the document Chattopadhyaya and Reese, *Chem. Soc. Chem. Comm.*, 1978, 639-640) and fluorenylmethyloxycarbonyl (Fmoc) groups.

By way of example of oligonucleotide synthesis conditions, reference may in particular be made to Current Protocols in Nucleic Acid Chemistry, Volume 1, Editors: S. L. Beaucage, D. E. Bergstrom, G. D. Glick, R. A. Jones, John Wiley & Sons, Inc., 2004; Protocols for oligonucleotides and analogs.

Generally, a method for oligonucleotide synthesis on a solid substrate comprises the following steps which correspond to the first cycle of the method:

1) providing a substrate on which a nucleoside bearing an —OH function which is protected, for example with a trityl, 4-O-monomethoxytrityl, 4,4'-O-dimethoxytrityl, tert-butyldimethylsilyl, acetyl, trifluoroacetyl, 9-phenylxanthen-9-yl or fluorenylmethyloxycarbonyl group, 2) deprotecting the hydroxyl function, by means of an acid treatment, for example using a solution of trichloroacetic acid or dichloroacetic acid, at a concentration of 2% to 3% by weight in a solvent such as dichloromethane, 3) adding a solution of a nucleotide synthon bearing a phosphoramidite function and a protected hydroxyl function, for example at a concentration of 0.05 to 0.2 M (=mol/L), in the presence of a coupling agent, such as tetrazole, ethylthiotetrazole, 4,5-dicyanoimidazole, saccharin 1-methylimidazole or 5-benzylthiotetrazole, for example at a concentration of 0.2 to 0.5 M, in a solvent such as acetonitrile, 4) blocking the hydroxyl functions which have not reacted with the reactive phosphorus-comprising functions, through the action of acetic anhydride or of phenoxyacetic anhydride which corresponds to milder conditions, optionally in the presence of methylimidazole or of dimethylaminopyridine, in a solvent such as tetrahydrofuran or a tetrahydrofuran/pyridine or tetrahydrofuran/lutidine mixture;

5) oxidizing the phosphorus through the action of an iodine solution, for example at a concentration of 0.02 to 0.1 M, for example in a tetrahydrofuran/pyridine/water mixture, or through the action of a peroxide, for example tert-butyl hydroperoxide, cumene hydroperoxide, hydrogen peroxide or bis-trimethylsilyl peroxide, for example at a concentration of 1 to 2 M in a decane/dichloromethane mixture, or through the action of a non-aqueous oxidizing agent, for instance (10-camphorsulfonyl)oxaziridine, for example at a concentration of 0.1 to 0.5 M in acetonitrile.

Conventionally, the amines of the nucleotide synthons used are protected, in order to avoid any parasitic reactions with the phosphorus-comprising functions of the nucleotide synthons reacted during the synthesis of the oligonucleotide (step 3). These protection techniques are well known to those skilled in the art. In particular, in the case of adenosine, the exocyclic amine function may be protected with a phenoxyacetyl group, in the case of cytidine, the exocyclic amino function may be protected with an acetyl group, in the case of guanosine, the exocyclic amino function may be protected with an isopropylphenoxyacetyl group, etc.

All these steps can be carried out at ambient temperature (22° C.). The nucleotides are protected throughout the nucleotide synthesis, according to methods well known to those skilled in the art.

Generally, steps 2), 3), 4) and 5) are followed by rinsing in order to remove the unreacted reagents.

Steps 2) to 5) are repeated as many times as necessary, with the selected nucleotide synthons which may vary from one cycle to another, so as to have the desired oligonucleotide sequence.

When a nucleotide synthon bearing a phosphodiester function is used, in step 3), the nucleotide synthon bearing a phosphodiester function is coupled in the presence of 1-mesitylenesulfonyl-3-nitro-1,2,4-triazole (MSNT) and of 1-methylimidazole. There is no oxidation step 5). Furthermore, at the end of the synthesis, prior to the final basic treatment, a treatment with a solution of syn-2-nitrobenzaldoxime and of 1,1,3,3-tetramethylguanidine in aqueous dioxane is carried out, as, for example, described in chapter 4 of the book edited by Gait, M., Oligonucleotide synthesis. A practical approach (1984) IRL Press, Oxford.

When a nucleotide synthon bearing a hydrogen phosphonate function is used, in step 3), the nucleotide synthon bearing a hydrogen phosphonate function is coupled in the presence of pivaloyl chloride in solution in acetonitrile. Steps 2) to 4) are repeated as many times as necessary so as to have the desired oligonucleotide sequence. Oxidation step 5) is carried out at the very end of synthesis.

Next, a final step in a basic medium is carried out, for example, either using a basic solution of sodium hydroxide, of aqueous ammonia or of potassium carbonate or a solution of methylamine and of aqueous ammonia or a solution of diisopropylamine and of β-mercaptoethanol, or using ammonia or methylamine in the gas phase. This basic treatment makes it possible to deprotect the nucleotides present in the oligonucleotide formed and, in the case of the method using phosphoramidite or hydrogen phosphonate synthons, also makes it possible to detach the formed oligonucleotide from the substrate. In the case of the method using phosphodiester synthons, this detachment takes place during the treatment with a mixture of syn-2-nitrobenzaldoxime and 1,1,3,3-tetramethylguanidine. More specifically, use may be made of either a basic solution of sodium hydroxide, for example at a concentration of 0.1 to 0.5 M of the nucleotides, in a solvent such as a water/methanol mixture, at a temperature of 15 to 80° C., or a solution of aqueous ammonia, for example at a concentration of 20 to 40% by weight, at a temperature of 15 to 65° C., or a solution of potassium carbonate, for example at a concentration of 0.02 to 0.1 M, in a solvent such as methanol, at a temperature of 15 to 30° C., or a solution of methylamine and aqueous ammonia (AMA), for example at a concentration of 10% to 20% by weight each, in a solvent such as water, at a temperature of 15 to 65° C., or a solution of 10% diisopropylamine/0.25 M β-mercaptoethanol in a solvent such as methanol, at a temperature of 45 to 65° C., or ammonia or methylamine in the gas phase, for example at a temperature of 15 to 30° C. Preferably, a basic treatment with a solution of potassium carbonate at a concentration of 0.02 to 0.1 M, in methanol, at a temperature of 15 to 30° C., is carried out.

In the context of the method according to the invention, it is possible to use, in step 1) of the first cycle, a substrate (Sa) in accordance with the invention, which will make it possible to introduce a diaminophenothiazinium derivative at the 3' end of the oligonucleotide synthesized.

It is also possible, during any cycle, to use a diaminophenothiazinium derivative (I), and in particular (Ia) or (Ib) in step 3) in place of the nucleotide synthon bearing a phosphoramidite function and a protected hydroxyl function. This makes it possible to integrate a diaminophenothiazinium derivative into the oligonucleotide, in place of a nucleotide. The use, in step 3) of the final cycle, of a diaminophenothiazinium derivative (Ic) will make it possible to introduce the diaminophenothiazinium group at the 3' end.

Of course, all these possibilities can be combined in order to incorporate various diaminophenothiazinium groups into the oligonucleotide formed.

The examples given hereinafter, with reference to the appended figures, illustrate the invention but are not limiting in nature.

Example 1

Figure 1:
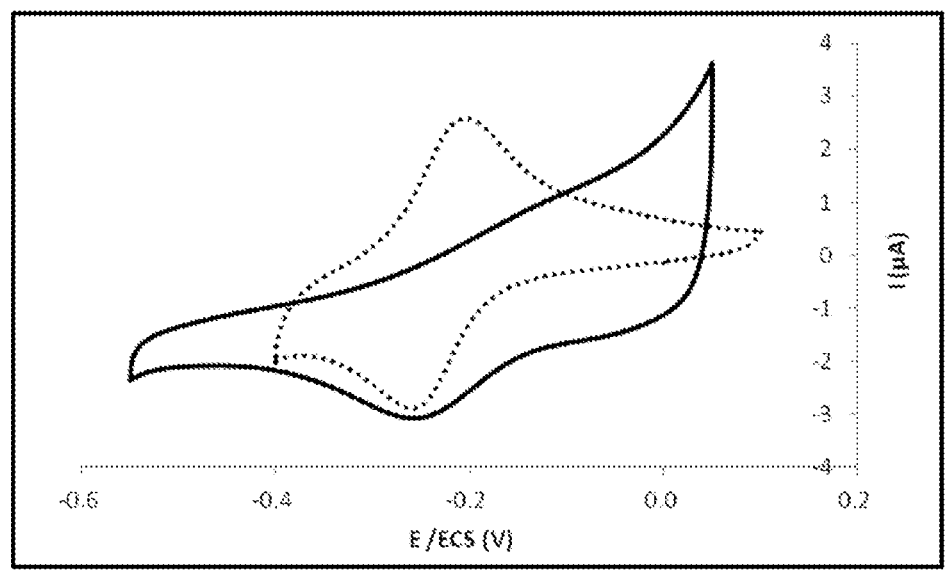
FIG. 1 shows the oxidoreduction potentials of methylene blue and of a compound according to the invention incorporated into an oligonucleotide in accordance with example 1.

Synthesis Of Dimethoxytrityl(Dibutyl-Diethanolamino)Phenothiazinium Phosphoramidite Dimethoxytrityl(dibutylamino)(diethanolamino)phenothiazinium phosphoramidite is prepared in accordance with SCHEME 1 below.

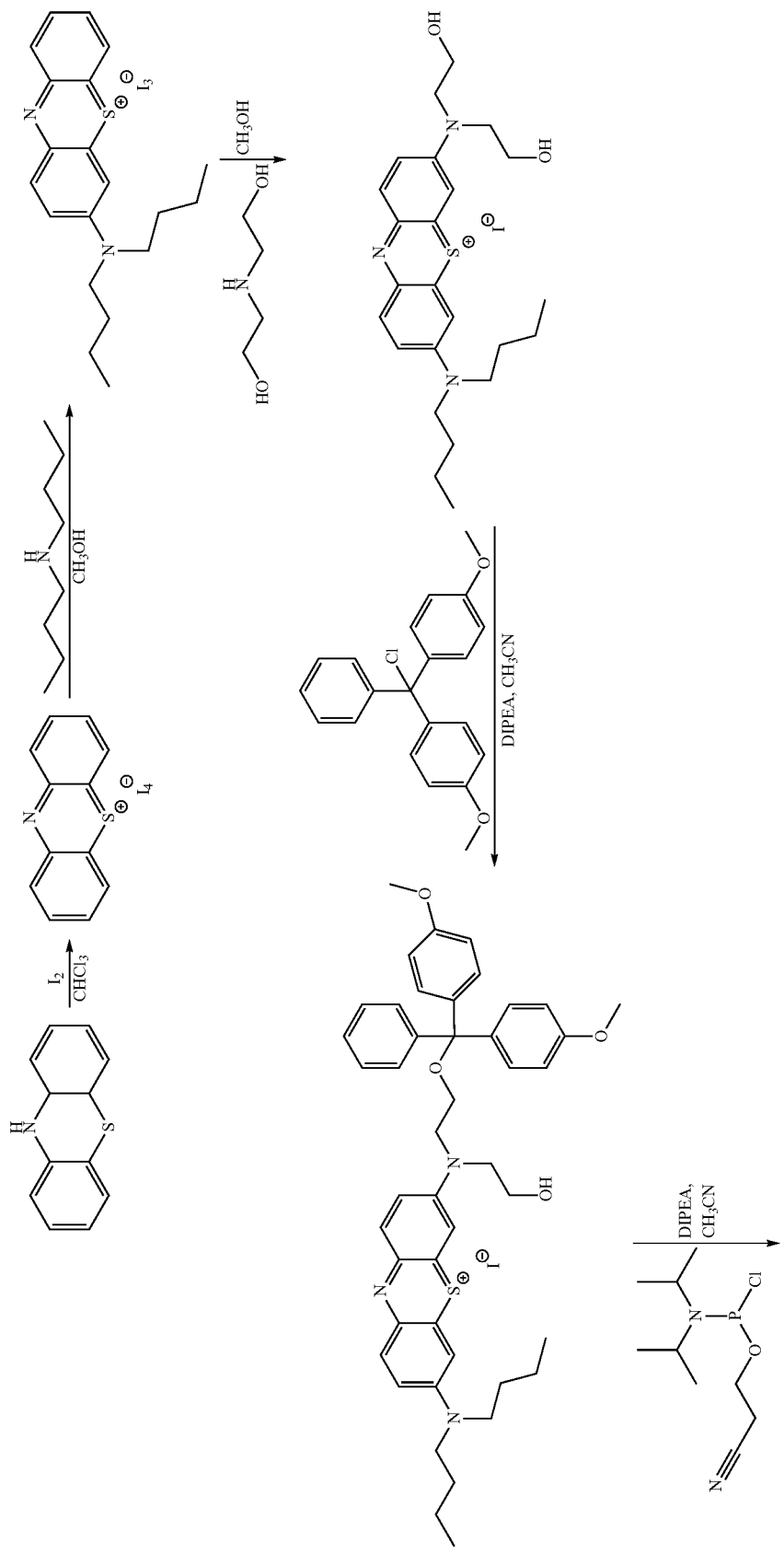

-continued
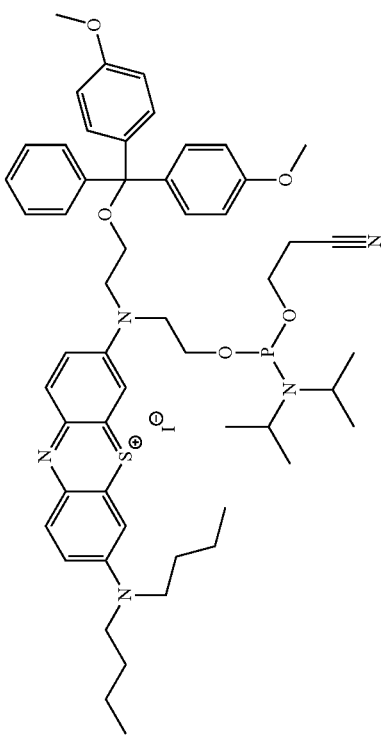

1) Preparation of phenothiazin-5-ium tetraiodide hydrate

A solution of iodine (15.2 g, 60 mmol) in chloroform (450 ml) is added dropwise for 2 h30 to a solution of phenothiazine (4.0 g, 20 mmol) in chloroform (120 ml), in a 1 l round-bottomed flask with magnetic stirring in an ice bath. Once the addition is complete, the mixture is stirred in an ice bath overnight.

The reaction mixture is filtered through sintered glass. The solid is washed with 900 ml of chloroform in order to remove the excess iodine. The solid is dried under reduced pressure for 2 h. A gray-purple powder is obtained with a quantitative yield (14.5 g, 20 mmol).

$^1$H NMR (DMSO-d6): δ (ppm)=8.06 (d, 2H); 7.92 (d, 2H); 7.73 (t, 2H); 7.61 (t, 2H)

MS (ESI+): mass calculated=198.0, mass measured=198.0

2) Preparation of (dibutylamino)phenothiazinium triiodide

The phenothiazinium tetraiodide (14.5 g, 20 mmol) is dissolved in 290 ml of methanol at ambient temperature. Dibutylamine (6.7 ml, 40 mmol, 2 eq) is added dropwise to the solution of phenothiazinium, with magnetic stirring. The reaction mixture is checked by TLC in an eluent consisting of a 95/5 (v/v) $CH_2Cl_2/CH_3OH$ mixture.

After reaction for 2 h, the mixture is filtered through sintered glass. A precipitate is recovered on the sintered glass, after washes with three times 30 ml of methanol. The solid is dried under reduced pressure for 1 h30. A gray-purple powder is obtained with a yield of 53% (7.45 g, 10.5 mmol).

$^1$H NMR (CD$_3$CN): δ (ppm)=8.25-7.55 (m, 7H, H arom.); 3.85 (m, 4H, 2×N—CH$_2$); 1.80 (m, 4H, 2×CH$_2$); 1.50 (m, 4H, 2×CH$_2$—CH$_3$); 1.01 (m, 6H, 2×CH$_3$)

MS (ESI+): mass calculated=325.2, mass measured=325.2

3) Preparation of (dibutylamino)(diethanolamino)phenothiazinium iodide

The (dibutylamino)phenothiazinium iodide (7.45 g, 10.5 mmol) is dissolved in 150 ml of methanol at ambient temperature (22° C.). A solution of diethanolamine (2.22 g, 21 mmol, 2 eq) diluted in methanol (35 ml) is prepared and then added dropwise using a dropping funnel to the solution of phenothiazinium, with magnetic stirring at ambient temperature. The reaction mixture is checked by TLC in an eluent consisting of a 9/1 (v/v) $CH_2Cl_2/CH_3OH$ mixture.

After reaction for 3 h, the mixture is concentrated in a rotary evaporator. The product is purified via silica gel chromatography (eluent 95/5, v/v, $CH_2Cl_2/CH_3OH$). A purple solid is obtained with a yield of 49% (2.85 g, 5.13 mmol).

$^1$H NMR (CD$_3$CN): δ (ppm)=7.90-7.22 (m, 6H, H arom.); 3.87 (m, 8H, 4×N—CH$_2$); 3.63 (m, 4H, 2×CH$_2$—OH); 1.71 (m, 4H, 2×N—CH$_2$—CH$_2$); 1.45 (m, 4H, 2×CH$_2$—CH$_3$); 1.01 (m, 6H, 2×CH$_3$)

MS (ESI+): mass calculated=428.2, mass measured=428.3

4) Preparation of dimethoxytrityl(dibutylamino)(diethanolamino)phenothiazinium iodide The (dibutylamino)(diethanolamino)phenothiazinium iodide (2.85 g, 5.13 mmol) is introduced into a 500 ml round-bottomed flask oven-dried beforehand. Anhydrous acetonitrile (300 ml) is added under an argon atmosphere. Diisopropylethylamine DIPEA (900 µl, 5.13 mmol, 1 eq) is added, and then a solution of chlorodimethoxytrityl (1.56 g, 4.62 mmol, 0.9 eq) in 80 ml of anhydrous acetonitrile is added dropwise with a syringe. The reaction mixture is stirred at ambient temperature. The reaction is monitored by TLC in 89/10/1, v/v/v, DCM/MeOH/TEA.

After 1 h30, the reaction is stopped by adding 1 ml of methanol. The solution is concentrated in a rotary evaporator. The product is purified by silica gel chromatography (eluent 94/5/1, v/v/v, $CH_2Cl_2/CH_3OH/Et_3N$). A purple solid is obtained with a yield of 52% (2.28 g, 2.66 mmol).

$^1$H NMR (CD$_3$CN): δ (ppm)=7.90-6.75 (m, 19H, H arom.); 3.75 (m, 4H, 2×N—CH$_2$); 3.66 (s, 6H, 2×O—CH$_3$); 3.66-3.45 (m, 8H, 2×N—CH$_2$ and 2×CH$_2$—OH); 1.70 (m, 4H, 2×N—CH$_2$—CH$_2$); 1.45 (m, 4H, 2×CH$_2$—CH$_3$); 1.01 (m, 6H, 2×CH$_3$)

MS (ESI+): mass calculated=730.4, mass measured=730.7

5) Preparation of dimethoxytrityl(dibutylamino)(diethanolamino)phenothiazinium phosphoramidite iodide (I.1)

The dimethoxytrityl(dibutylamino)(diethanolamino)phenothiazinium iodide (2.28 g, 2.66 mmol) is coevaporated twice from 20 ml of anhydrous acetonitrile, and then taken up in 50 ml of anhydrous acetonitrile. Diisopropylethylamine (930 µl, 5.32 mmol, 2 eq) is added under an argon atmosphere, and then chlorophosphine (710 µl, 3.19 mmol, 1.2 eq) is added dropwise with a syringe. The reaction mixture is stirred at ambient temperature. The reaction is monitored by TLC in 49/49/2, v/v/v, $CH_2Cl_2/CH_3CN/Et_3N$.

After reaction for 30 min, the solution is concentrated in a rotary evaporator. The product is purified by silica gel chromatography (eluent 99/1 $CH_2Cl_2/Et_3N$). A purple oil is obtained with a yield of 26% (743 mg, 0.70 mmol).

$^{31}$P NMR (CD$_3$CN): δ (ppm)=149.3

MS (ESI+): mass calculated=930.5, mass measured=930.5

6) Synthesis of an oligonucleotide labeled with the (dibutylamino)(diethanolamino)phenothiazinium derivative This example illustrates the incorporation of dimethoxytrityl (dibutylamino)(diethanolamino)phenothiazinium phosphoramidite iodide (compound I.1) into the synthesis of an oligonucleotide of formula: 5'-d(XGG GAAAGGGAGAAGACGTCCAAAAACTTTCCCYY)-3'.

In this sequence, A represents adenosine, C cytidine, G guanosine, T thymidine, X (dibutylamino)(diethanolamino)phenothiazinium and Y 1,2-dithiane which will allow the grafting of the oligonucleotide onto a gold surface for the electrochemical characterizations. The synthesis is carried out using the corresponding phosphoramidite synthons protected in the 5' position with a dimethoxytrityl group. For adenosine, the exocyclic amino function is protected with the phenoxyacetyl group. For cytidine, the exocyclic amino function is protected with the acetyl group. For guanosine, the exocyclic amino function is protected with the isopropylphenoxyacetyl group.

The synthesis was carried out by means of an Applied Biosystems DNA/RNA 394 automatic oligonucleotide synthesizer using:

1 μmol of a dithiane dialcohol molecule (4-O-dimethoxytrityl cyclodithioerythritol) grafted onto a "Controlled Pore Glass" substrate functionalized with aminated chains, the bond between the 4-O-dimethoxytrityl cyclodithioerythritol and the amine being produced by a succinyl radical as described in the article by P. Liepold, T. Kratzmüller, N. Persike, M. Bandilla, M. Hinz, H. Wieder, H. Hillebrandt, E. Ferrer, G. Hartwich, Anal. Bioanal. Chem. (2008) 391:1759-1772;

15 μmol of (dibutylamino)(diethanolamino)phenothiazinium or of synthons of adenosine, cytidine, guanosine, thymidine or dithiane, per synthesis cycle according to the preprogrammed sequence.

In a first step, the dimethoxytrityl group of the dithiane molecule grafted onto the CPG is cleaved by means of a treatment with trichloroacetic acid at 3% by weight in dichloromethane, at ambient temperature for 120 s, freeing a hydroxyl function.

In a second step, a synthon bearing a phosphoramidite function and a hydroxyl function protected with a dimethoxytrityl group, at a concentration of 0.1 M in acetonitrile, is coupled, in the presence of tetrazole at a concentration of 0.45 M in acetonitrile, at ambient temperature, for 30 s for the phosphoramidites A, T, C and G, 360 s for the dithiane phosphoramidite and 60 s for the (dibutylamino)(diethanolamino)phenothiazinium phosphoramidite.

In a third step, the hydroxyl functions which did not react in the previous step are blocked with a solution of phenoxyacetic anhydride/pyridine/tetrahydrofuran (1:1:8), in the presence of methylimidazole at 16% by weight in tetrahydrofuran, at ambient temperature for 20 s.

In a fourth step, the phosphite triester is oxidized to phosphate triester using a solution of iodine at a concentration of 0.02 M in a water/pyridine/tetrahydrofuran (1:2:7) mixture, at ambient temperature for 30 s.

The four steps are repeated as many times as required by the programmed sequence.

At the end of the synthesis, the oligonucleotide is detached from the substrate by treatment with potassium carbonate at 0.05 M in anhydrous methanol (1 ml) at ambient temperature for 6 h. The solution is then neutralized by adding 1.5 ml of 2 M tetraethylammonium acetate in water, and then filtered through Amicon 3K filters (Millipore) in order to remove the salts and compounds resulting from the deprotection of the oligonucleotide.

The oligonucleotide is purified by high performance liquid chromatography (HPLC) on a Licrospher RP18 reverse phase column. The elution of the oligonucleotide labeled with the phenothiazinium derivative is monitored by visible absorption at 677 nm. The corresponding fractions are collected and concentrated in a SpeedVac evaporator.

The product is analyzed by MALDI-ToF mass spectrometry by cocrystallization in a 3-hydroxypicolinic acid matrix. The mass measured (18813 Da) corresponds to the mass calculated (18814 Da), which proves that the phenothiazinium derivative was not degraded under the oligonucleotide synthesis and deprotection conditions.

7) Oxidoreduction Data

A comparison of the oxidoreductive properties of dimethylamino phenothiazinium (methylene blue) and of the (dibutylamino)(diethanolamino) phenothiazinium synthon incorporated onto an oligonucleotide is carried out using an electrochemical cell consisting of a gold working electrode, a platinum counterelectrode and a saturated calomel reference electrode. The technique used is cyclic voltammetry. The buffer used is a 20 mM $Na_2HPO_4/KH_2PO_4$ buffer containing 250 mM KCl, of pH 6.7.

The methylene blue (dashed-line curve) is studied in solution (concentration 15.6 μM). The modified synthon (solid-line curve) is studied after grafting onto the gold electrode with a solution containing 2 nmol of the labeled oligonucleotide. It is observed in FIG. 1 that the two curves show similar reduction and oxidation potentials.

Example 2

Synthesis of Dimethoxytrityl Bis(butylbutanolamino)phenothiazinium Phosphoramidite 1) Preparation of bis(butylbutanolamino)phenothiazinium iodide Phenothiazinium tetraiodide (145 mg, 0.2 mmol) is dissolved in 4 ml of methanol at ambient temperature. Butylbutanolamine (115 μl, 1 mmol, 5 eq) is added dropwise to the phenothiazinium solution, with magnetic stirring. The reaction mixture is checked by TLC in an eluent consisting of a 9/1 (v/v) $CH_2Cl_2/CH_3OH$ mixture.

After reaction for 2 h, the solution is concentrated in a rotary evaporator. The product is purified by silica gel chromatography (eluent 95/5, v/v, $CH_2Cl_2/CH_3OH$). A purple oil is obtained with a yield of 41% (50 mg, 0.08 mmol).

$^1$H NMR ($CD_3CN$): δ (ppm)=7.90-7.23 (m, 6H, H arom.); 3.60 (m, 8H, 4×N—$CH_2$); 3.00 (m, 4H, 2×$\underline{CH_2}$—OH); 1.90-1.55 (m, 12H, 6×$CH_2$); 1.50-1.32 (m, 4H, 2×$\underline{CH_2}$—$CH_3$); 0.99 (m, 6H, 2×$CH_3$)

MS (ESI+): mass calculated=484.3, mass measured=484.3

2) Preparation of dimethoxytrityl bis(butylbutanolamino)phenothiazinium phosphoramidite iodide (I.1)

This compound is prepared as in example 1), 4) and 5).

Example 3

Stability Study

Figure 2:
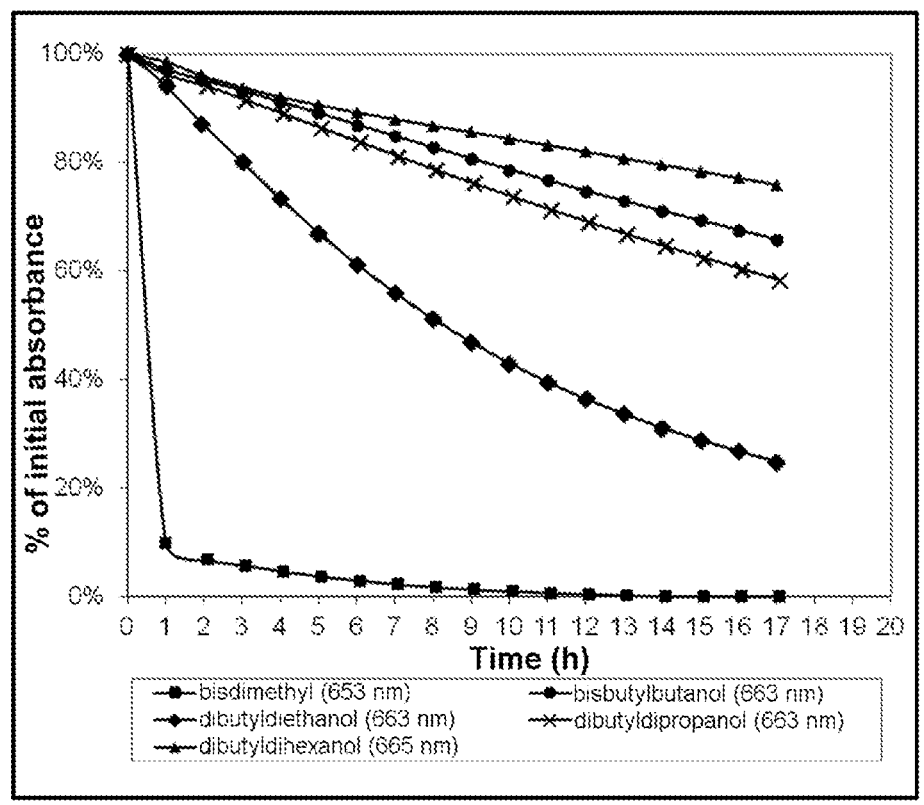
FIG. 2 shows the change in the absorbance percentages as a function of time of various bisaminophenylthiazinium derivatives, in a basic medium.

It was demonstrated that, by incorporating a dibutylamine and a diethanolamine or two butylbutanolamines, a significant gain in stability in a solution of $K_2CO_3$ (0.05M) in methanol is obtained compared with the bis(dimethylamino) phenothiazinium iodide compound (methylene blue salt) as illustrated in FIG. 2.

The TABLE below also demonstrates the gains in stability obtained with amines other than the dimethylamines present on methylene blue.

TABLE

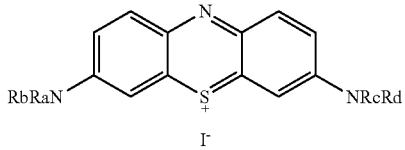

| Molecules | Stability after treatment in 0.05M K$_2$CO$_3$/MeOH | |
|---|---|---|
| | 4 h | 17 h |
| Methylene blue Ra=Rb=Rc=Rd=methyl | 5% | 0% |
| Ra=Rb=Rc=Rd=ethyl | 84% | 67% |
| Ra=Rb=Rc=Rd=(2-ethyl)hexyl | 92% | 74% |
| Ra=Rb=Rc=Rd=butyl | 92% | 78% |
| Ra=Rc=butyl and Rb=Rd=butanol | 91% | 66% |
| Ra=Rb=butyl and Rc=Rd=ethanol | 73% | 25% |
| Ra=Rb=butyl and Rc=Rd=propanol | 89% | 58% |
| Ra=Rb=butyl and Rc=Rd=hexanol | 92% | 76% |

The invention claimed is:

1. Diaminophenothiazinium derivatives of formula (I):

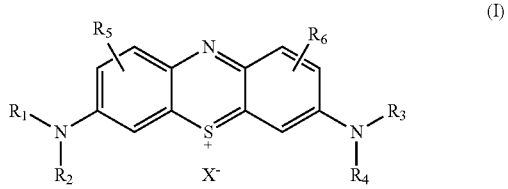

in which:
one of the $R_1$, $R_2$, $R_3$ and $R_4$ groups represents -$A_1$-$OR_7$, with $A_1$ representing a linear or branched alkylene chain comprising from 2 to 12 carbons, the oxygen and nitrogen atoms being separated by at least two consecutive carbon atoms, and $R_7$ representing a group forming, with $OA_1$ to which it is bonded, a phosphoramidite, phosphodiester, or a hydrogen phosphonate group,
the other $R_1$, $R_2$, $R_3$ and $R_4$ groups, which may be identical or different, represent, independently of one another:
an -$A_2$-$OR_8$ group, with $A_2$ representing a linear or branched alkylene chain comprising from 2 to 12 carbons, the oxygen and nitrogen atoms being separated by at least two consecutive carbon atoms, and $R_8$ representing a member selected from the group consisting of trityl, 4-O-monomethoxytrityl, 4,4'-O-dimethoxytrityl, tert-butyldimethylsilyl, acetyl, trifluoroacetyl, 9-phenylxanthen-9-yl, and fluorenylmethyloxycarbonyl,
an alkyl group having from 2 to 12 carbon atoms,
or, $R_1$ and $R_2$ or $R_3$ and $R_4$ are bonded to one another to form, with the nitrogen atom to which they are bonded, a piperidinyl or pyrrolidinyl group,
$R_5$ and $R_6$, which may be identical or different, represent, independently of one another, a hydrogen, chlorine, bromine, iodine or fluorine atom, or an alkyl group having from 1 to 12 carbon atoms, an alkenyl group having from 2 to 12 carbon atoms, an alkynyl group having from 2 to 12 carbon atoms, an acyl group or a phenyl group, and
$X^-$ represents an anion.

2. The diaminophenothiazinium derivatives as claimed in claim 1, characterized in that $A_1$ and $A_2$ are linear or branched alkylene chains in which from 2 to 6 consecutive carbon atoms separate the oxygen and nitrogen atoms.

3. The diaminophenothiazinium derivatives as claimed in claim 1, characterized in that at least one of the $R_1$, $R_2$, $R_3$ and $R_4$ groups does not represent an -$A_2$-$OR_8$ group, as defined in claim 1, and said $R_1$, $R_2$, $R_3$, or $R_4$ group(s) are different than -$A_1$-$OR_1$ and wherein -$A_2$-$OR_8$ represent(s) an alkyl group having from 2 to 12 carbon atoms.

4. The diaminophenothiazinium derivatives as claimed in claim 1, wherein $R_5$=$R_6$=H.

5. The diaminophenothiazinium derivatives as claimed in claim 1, wherein $R_7$ represents a —P{N[(C$_2$-C$_{12}$)alkyl]$_2$}(OCH$_2$CH$_2$C≡N) group.

6. The diaminophenothiazinium derivatives as claimed in claim 5, wherein $R_7$ represents the —P[N ($^i$Pr)$_2$](OCH$_2$CH$_2$C≡N) group.

7. The diaminophenothiazinium derivatives as claimed in claim 1, of formula (Ia):

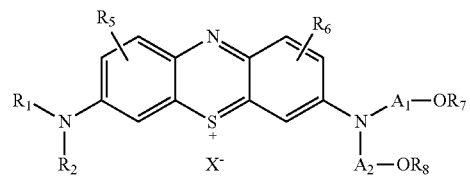

in which:
$A_1$, $A_2$, $R_5$, $R_6$, $R_7$, $R_8$ and $X^-$ are as defined in claim 1,
$R_1$ and $R_2$, which may be identical or different, represent, independently of one another, an alkyl group having from 2 to 12 carbon atoms, or $R_1$ and $R_2$ are bonded to one another to form, with the nitrogen atom to which they are bonded, a piperidinyl or pyrrolidinyl group.

8. The diaminophenothiazinium derivatives as claimed in claim 1, of formula (Ib):

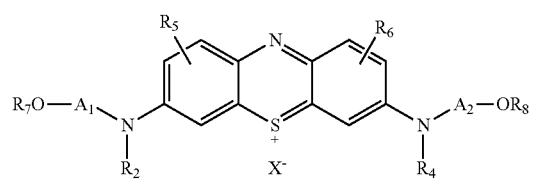

in which:
$A_1$, $A_2$, $R_5$, $R_6$, $R_7$, $R_8$ and $X^-$ are as defined in claim 1,
$R_2$ and $R_4$, which may be identical or different, represent, independently of one another, an alkyl group having from 2 to 12 carbon atoms.

9. The diaminophenothiazinium derivatives as claimed in claim 1, of formula (Ic):

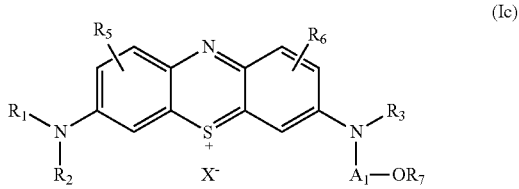

in which:
$A_1$, $R_5$, $R_6$, $R_7$ and $X^-$ are as defined in claim 1,
$R_1$ and $R_2$, which may be identical or different, represent, independently of one another, an alkyl group having from 2 to 12 carbon atoms, or $R_1$ and $R_2$ are bonded to one another to form, with the nitrogen atom to which they are bonded, a piperidinyl or pyrrolidinyl group, $R_3$ represents an alkyl group having from 2 to 12 carbon atoms.

10. The diaminophenothiazinium derivatives as claimed in claim 1, wherein $X^-$ is selected from the group consisting of $Cl^-$, $I^-$, $ClO_4^-$, and $NO_3^-$.

11. A method for labeling an oligonucleotide with a diaminophenothiazinium derivative as claimed in claim 1, which comprises the growth of an oligonucleotide grafted onto a solid substrate, and the replacement of one or more of the nucleotides of which it is formed with one or more of said diaminophenothiazinium derivatives, before the oligonucleotide is detached from the solid substrate.

12. The labeling method as claimed in claim 11, wherein at least one replacement with a diaminophenothiazinium derivative is carried out before the end of the growth of the oligonucleotide.

13. The labeling method as claimed in claim 11, wherein at least one substitution with a diaminophenothiazinium derivative is carried out in the 3' or 5' positions, on the first or the last nucleotide, respectively.

14. The labeling method as claimed in claim 11, comprising a final step of treatment in a basic medium, either using a basic solution of sodium hydroxide, of aqueous ammonia, or of potassium carbonate, or a solution of methylamine and of aqueous ammonia, or a solution of diisopropylamine and of β-mercaptoethanol, or using ammonia or methylamine in the gas phase.

15. Labeled oligonucleotides obtained by the method of claim 11.

16. An oligonucleotide synthesis substrate comprising at least one diaminophenothiazinium derivative covalently grafted at the surface according to the series:

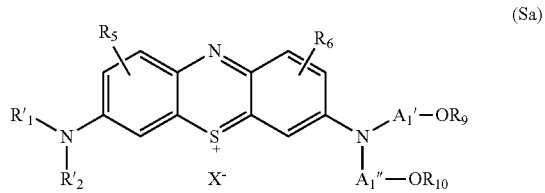

(Sa)

in which:

$R_5$, $R_6$, which may be identical or different, represent, independently of one another, a hydrogen, chlorine, bromine, iodine, or fluorine atom, or an alkyl group having from 1 to 12 carbon atoms, an alkenyl group having from 2 to 12 carbon atoms, an alkynly group having from 2 to 12 carbon atoms, an acyl group, or a phenyl group, $X^-$ represents an anion, $R'_1$ and $R'_2$, identical or different, represent, independently of one another, an alkyl group having from 2 to 12 carbon atoms, or $R_1$ and $R_2$ are bonded to one another to form, with the nitrogen atom to which they are bonded, a piperidinyl or pyrrolidinyl group, $A_1'$ and $A_1''$, which may be identical or different, represent, independently of one another, a linear or branched alkylene chain comprising from 2 to 12 carbons, and $R_9$ represents a member selected from the group consisting of trityl, 4-O-monomethoxytrityl, 4, 4'-O-dimethoxytrityl, tert-butyldimethylsilyl, acetyl, trifluoroacetyl, 9-phenylxanthen-9-yl, and fluorenylmethyloxycarbonyl; and $R_{10}$ represents —CO-$A_3$-CO—NH-Substrate, with $A_3$ representing a linear or branched alkylene chain comprising from 1 to 6 carbon atoms; or

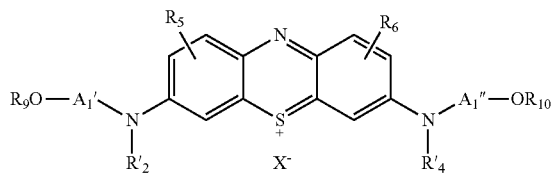

(Sb)

in which:

$R_5$, $R_6$, which may be identical or different, represent, independently of one another, a hydrogen, chlorine, bromine, iodine or fluorine atom, or an alkyl group having from 1 to 12 carbon atoms, alkenyl group having from 2 to 12 carbon atoms, an alkynyl group having from 2 to 12 carbon atoms, an acyl group or a phenyl group, $X^-$ represents an anion, $R'_2$ and $R'_4$, which may be identical or different, represent, independently of one another, and alkyl group having from 2 to 12 carbon atoms, $A_1'$ and $A_1''$, which may be identical or different, represent, independently of one another, a linear or branched alkylene chain comprising from 2 to 12 carbons, and $R_9$ represents a member selected from the group consisting of trityl, 4-O-monomethoxytrityl, 4, 4'-O-dimethoxytrityl, tert-butyldimethylsilyl, acetyl, trifluoroacetyl, 9-phenylxanthen-9-yl, and fluorenylmethyloxycarbonyl; and $R_{10}$ represents —CO-$A_3$-CO—NH-Substrate, with $A_3$ representing a linear or branched alkylene chain comprising from 1 to 6 carbon atoms.

17. The oligonucleotide synthesis substrate as claimed in claim 16, wherein the substrate is selected from resins based on a member selected from the group consisting of polystyrene, polyacrylamide, polyethylene glycol, cellulose, polyethylene, polyester, latex, polyamide, polydimethylacrylamide, synthetic or natural hydrophilic polymers, glasses and silicas with a controlled porosity, glass beads or silica gels.

18. An oligonucleotide synthesis substrate as claimed in claim 16, wherein $R_5=R_6=H$.

19. An oligonucleotide synthesis substrate as claimed in claim 16, wherein $X^-$ is selected from the group consisting of $Cl^-$, $I^-$, $ClO_4^-$, and $NO_3^-$.

* * * * *